(12) United States Patent
Almodovar (10) Patent No.: US 9,730,689 B2
(45) Date of Patent: Aug. 15, 2017

(54) ROTATIONAL ACTION NEEDLE DRIVER (71) Applicant: Luis Jose Almodovar, San Juan, PR (US)

(72) Inventor: Luis Jose Almodovar, San Juan, PR (US)

(*) Notice: Subject to any disclaimer, the term of this patent is extended or adjusted under 35 U.S.C. 154(b) by 0 days.

(21) Appl. No.: 14/949,877

(22) Filed: Nov. 23, 2015

(65) Prior Publication Data

US 2016/0074032 A1 Mar. 17, 2016

Related U.S. Application Data

(63) Continuation-in-part of application No. 12/554,795, filed on Sep. 4, 2009, now Pat. No. 9,192,376.

(51) Int. Cl.
| | |
|---|---|
| *A61B 17/062* | (2006.01) |
| *A61B 17/00* | (2006.01) |
| *A61B 17/04* | (2006.01) |
| *A61B 17/29* | (2006.01) |
| *A61B 90/00* | (2016.01) |
| *A61B 17/28* | (2006.01) |

(52) U.S. Cl.
CPC ........ *A61B 17/062* (2013.01); *A61B 17/0491* (2013.01); *A61B 2017/0042* (2013.01); *A61B 2017/2837* (2013.01); *A61B 2017/2929* (2013.01); *A61B 2017/2946* (2013.01); *A61B 2090/067* (2016.02)

(58) Field of Classification Search
CPC .............. A61B 17/062; A61B 17/0492; A61B 2017/2837; A61B 2017/2946; A61B 2017/2929

See application file for complete search history.

(56) References Cited

U.S. PATENT DOCUMENTS

| 1,108,737 | A | * | 8/1914 | Gajdos | ................. | A61B 17/062 |
|---|---|---|---|---|---|---|
| | | | | | | 606/147 |
| 7,588,583 | B2 | | 9/2009 | Hamilton et al. | | |
| 8,252,007 | B2 | | 8/2012 | Hamilton et al. | | |
| 8,317,805 | B2 | | 11/2012 | Hamilton et al. | | |
| 8,603,113 | B2 | | 12/2013 | Hamilton et al. | | |
| 2014/0222036 | A1 | | 8/2014 | Hamilton et al. | | |

* cited by examiner

*Primary Examiner* — Kathleen Holwerda
(74) *Attorney, Agent, or Firm* — Eugenio J. Torres-Oyola; Victor Rodriguez-Reyes; Ferraiuoli LLC (57) ABSTRACT

A rotational action needle driver that comprises an cumbersome ergonomically designed handle, rotational mechanism and an integrated locking/unlocking system that permits surgeons to perform the surgical suturing procedure in a less complicated and more secure way by allowing more control over the suturing needle and the area to be stitched, even when the suturing area is small, deep, and/or restricted.

5 Claims, 9 Drawing Sheets

ROTATIONAL ACTION NEEDLE DRIVER

RELATED APPLICATIONS

This application is related to U.S. patent application Ser. No. 12/554,795 filed on Sep. 4, 2009 now U.S. Pat. No. 9,192,376.

STATEMENT REGARDING FEDERALLY SPONSORED RESEARCH AND DEVELOPMENT

N/A

BACKGROUND OF INVENTION

Field of the Invention

The present invention relates generally to a surgical suturing device, more specifically, to an ergonomic rotational action needle driver which enhance the tissue suturing procedure, particularly the one performed on restricted, deep and less accessible locations.

Background of the Invention

Surgical procedures have proliferated among the medical practice as new treatments are developed to effectively treat common and extraordinary conditions. The spectrum of invasiveness goes from simple tissue suturing of small open wounds to complicated procedures as those performed in vascular or neurological surgeries. It is undoubted that each and every step on any surgical procedure is of great importance and could cause negative consequences for the patient if it is inadequately performed. The suturing procedure, in particular, could end in serious consequences for the patient if negligently conducted, causing damages to adjacent tissues or even organs.

It is known that the suturing procedure consumes a considerable amount of time of the surgical treatment. Simplification of the suturing procedure by developing more effective suturing devices will reduce the time spent on that task and at the same time will reduce the risk of negative consequences arising from damages caused to adjacent tissues or organs.

Generally, the instruments used in suturing procedures are the suturing material, the suturing needle and the suturing driver. Efforts made to reduce the suturing time and to enhance the suturing procedures' safety have been focused on performing needle driver's modifications. One of the generally unattended deficiencies of the available needle drivers is the handedness of its designs. Some of the deficiencies were attended by U.S. patent application Ser. No. 12/554,795 filed on Sep. 4, 2009 now U.S. Pat. No. 9,192,376. The entire content of U.S. Pat. No. 9,192,376 are hereby incorporated by reference.

However there is a need to provide a less cumbersome mechanism for a rotational driver rotational action needle driver. Therefore the present invention provides a more efficient simple mechanism as a rotational action needle driver.

SUMMARY OF THE INVENTION

The disclosed embodiment of the present invention helps provide an effective suturing device that enhances the maneuvering and safety of suturing procedures. The disclosed invention consists of a suturing needle driver that comprises an ergonomical handle that eases the suturing process. It also comprises a rotational mechanism that permits users to maintain the needle tightly fixed to the needle driver in order to have a best control over the needle and the movements related to the suturing process. It permits the user to position the suturing needle at the exact angle at which the suturing material has to be inserted into the tissue.

Therefore, it can be appreciated that there exist a prevalent necessity for new and improved ergonomical suturing device to perform safest and simplest suturing procedures. The present disclosure overcomes the inability of the prior art to foresee the need of an less cumbersome suturing needle driver that permits users to performed safe suturing procedures.

Another deficiency presented by the prior art is the lack of disclosure of needle driver having a rotational mechanism that permits to fix the needle to a specific angle before inserting it into the tissue and combining the said rotation with ergonomic characteristics in order to facilitate the suturing processes.

In light of the foregoing, it will be appreciated that what is needed in the art is a suturing needle driver lacking of handedness and combining a rotational mechanism. Thus, the object of the present invention is to provide a surgical device that eases the suturing procedure associated with deep, restricted areas.

Another object of the present invention is to provide a surgical suturing needle driver that permits to grasp, secure and rotate a curved surgical needle without requiring a rotational motion at the surgeon's wrist.

It is the object of the present invention to provide a surgical suturing needle driver which incorporates a rotational mechanism that secures the needle to the needle driver and permits to diminish the number of maneuvers actually needed for performing the surgical suturing process, reducing the risk of damaging peripheral tissues.

It is a further object of the present invention to provide an ergonomically designed suturing needle driver that eliminates the difficulties associated with needle driver maneuvering that arise from the handedness of that kind of instrument.

The system of the disclosure itself, both as to its configuration and its mode of operation will be best understood, and additional objects and advantages thereof will become apparent, by the following detailed description of a preferred embodiment taken in conjunction with the accompanying drawing.

DESCRIPTION OF THE PREFERRED EMBODIMENT

Figure 1:
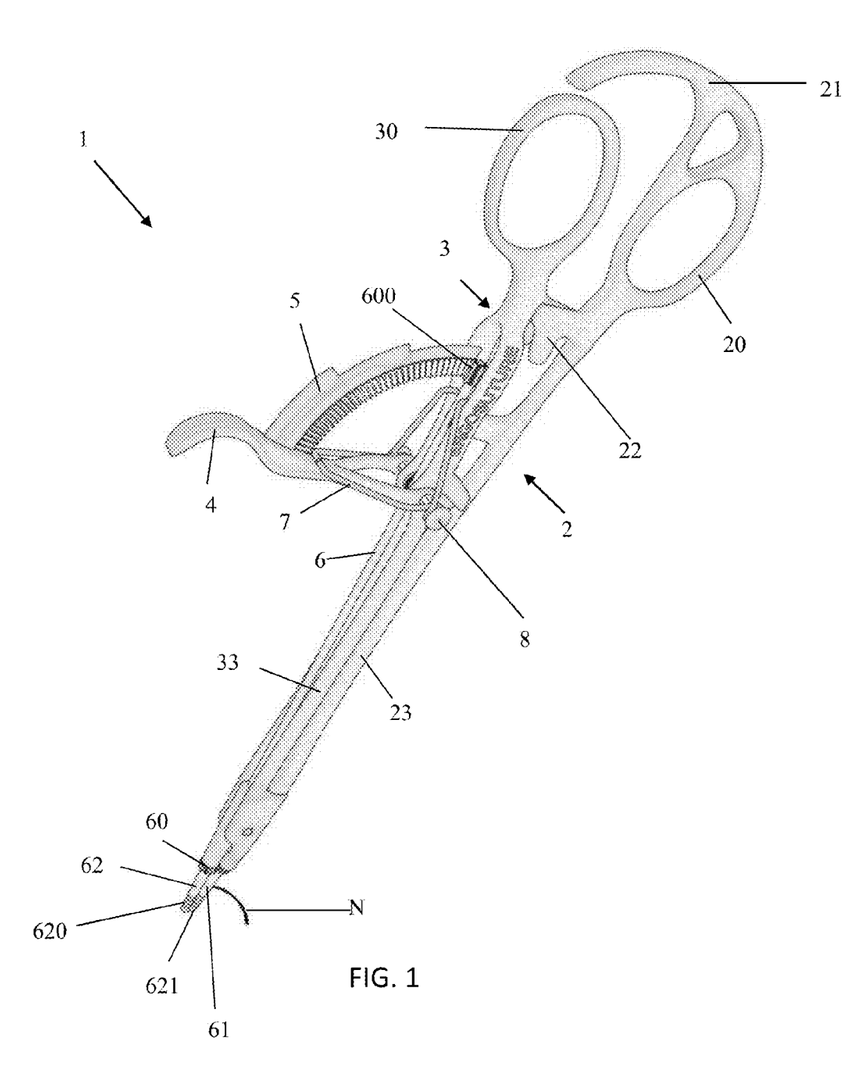
FIG. 1 shows a perspective view of the exemplary embodiment in accordance according with the principles of the present disclosure.

Turning to the diagram, FIG. 1 shows the device 1 of the present disclosure comprises a first elongated element 2, a second elongated element 3, an actuator 4 and rotational transfer element 6 and at least an elastic member 7.

The first elongated element 3, as shown in FIG. 2A-3B, includes a first elongated body 33, a first tip 61 at a distal end and a round contour including a first socket 30 at the proximal end. The second elongated element 2, as shown in FIG. 2B, includes a second elongated body 23, a second tip 62 at a distal end and a round contour including a second socket 20 at the proximal end. The rounded contour of the first elongated element 3 and second elongated element 2 are ergonomically designed to rest against surgeon's palm his hand, permitting its proper use to right and left handed surgeons, therefore a resting palm wall 21 is provided coupled to the first socket 20 at the proximal end. The surgeon will maintain the handle fixed to the palm his hand by using his thumb.

The present device comprises several features presented from FIG. 1 through FIG. 11B. For example, an object of the present disclosure is to perform safest and simplest suturing procedures. The present suturing device 1 comprises a suturing mechanism including an actuator 4, wherein said actuator 4 initiates the rotational mechanism during the suturing procedure using the present device 1.

Figures 2A, 2B:
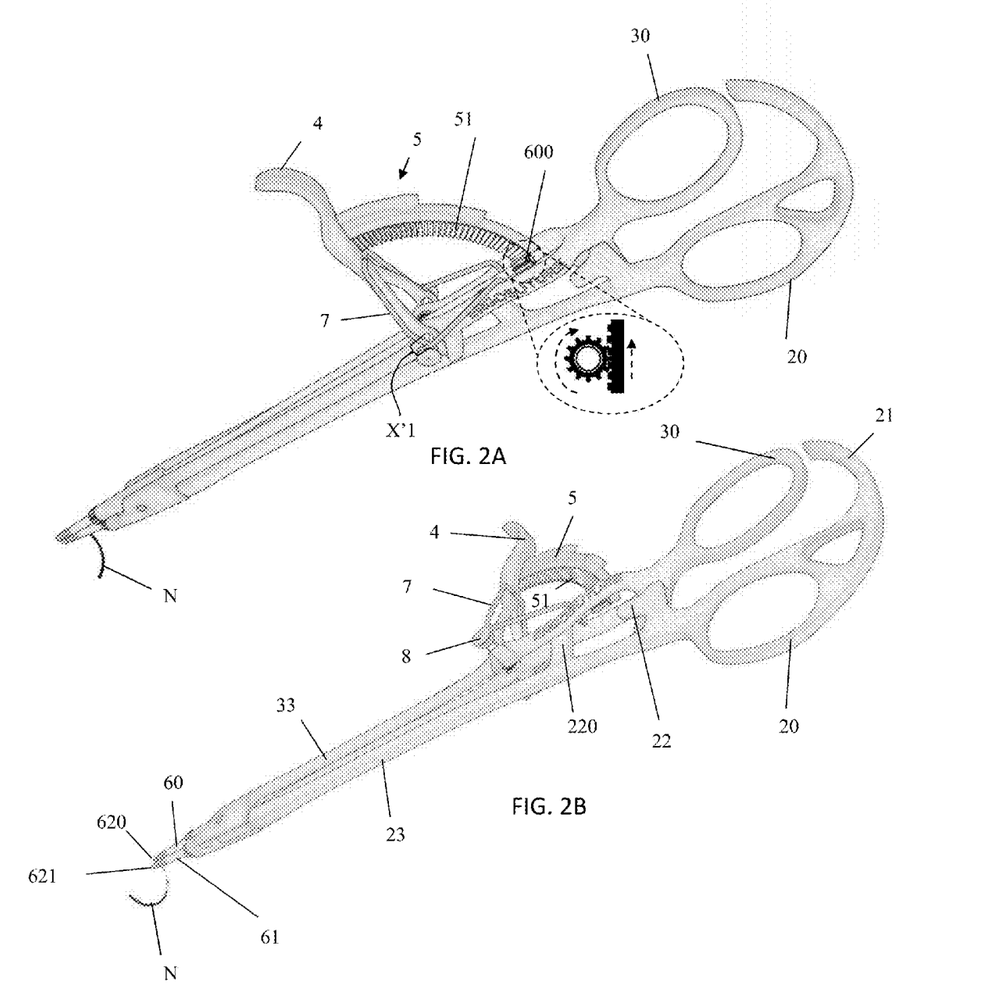
FIGS. 2A and 2B shows perspective views of the exemplary embodiment with actuator at a first position in accordance according with the principles of the present disclosure.
Figures 3A, 3B:
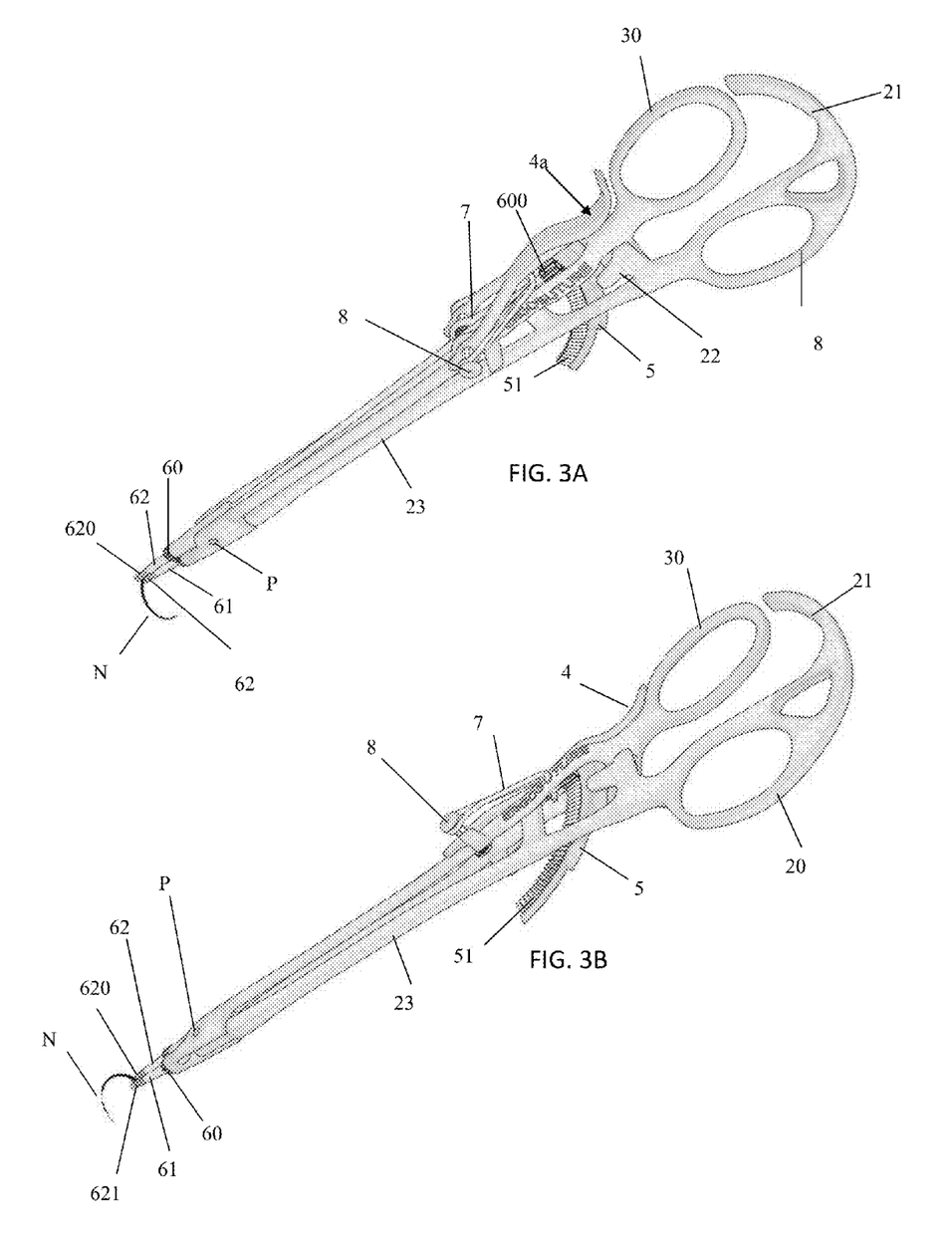
FIGS. 3A and 3B shows perspective views of the exemplary embodiment with actuator at second position in accordance according with the principles of the present disclosure.

In accordance with the principles of the current disclosure the actuator 4 is mechanically coupled to the first elongated element 3 at a first pivot point, as shown in 2A through 3B. The actuator 4 is mechanically coupled to the first elongated body 33 by a pin 8, wherein said pin 8 permits rotational movement or displacement of said actuator 4 with respects to said first pivot point. The actuator 4 comprises a platform 4A, mainly extended away from the first elongated body 33, configured or shaped to receive a thumb and be driven by said thumb, Base on the present exemplary embodiment the actuator is driven by the thumb, wherein said thumb pushes said platform 4A towards the first elongated body 33 moving the actuator from a first position, as shown in FIGS. 2A-2B, to a second position, as shown in FIGS. 3A-3B. It is important to understand that the movement of the actuator 4 is a radial displacement wherein the center said radial displacement is provided by the first pivot point or pin 8.

Further the actuator 4 comprises a linear actuator mechanism fixed to said platform 4A, wherein said linear actuator comprises a rack 51, which moves mainly vertical toward the first elongated body 33. The rack 51 is configured or designed to interact with the rotational bar 6, more particularly with the pinion 600 at a distal end of said rotational bar 6, as shown in FIG. 2A through 3B. The interaction of the rack and pinion converts the radial displacement of the actuator 4 into a rotational movement of the rotational bar 6. The rotational bar 6 structures is explained in more details below.

Figure 4A:
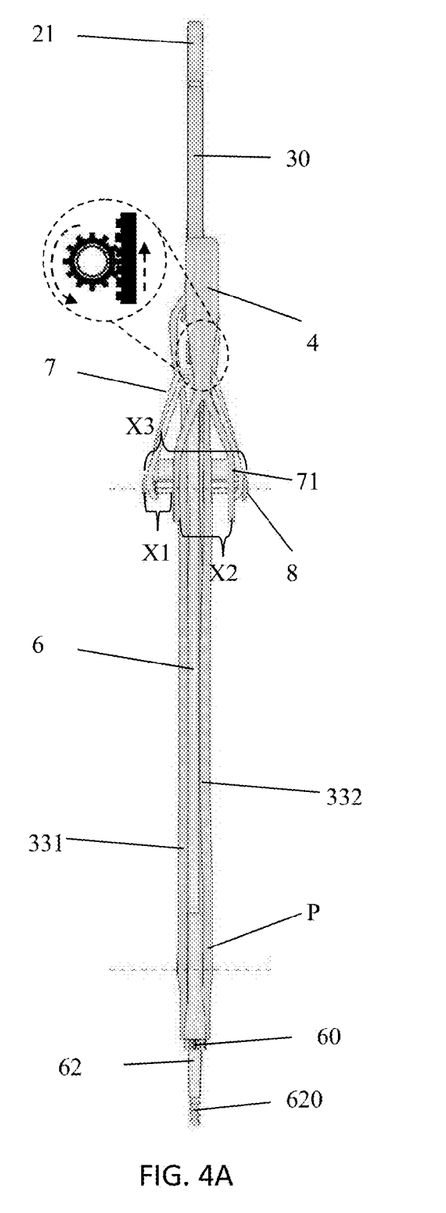
FIGS. 4A and 4B shows side views of the exemplary embodiment in accordance according with the principles of the present disclosure.
Figure 4B:
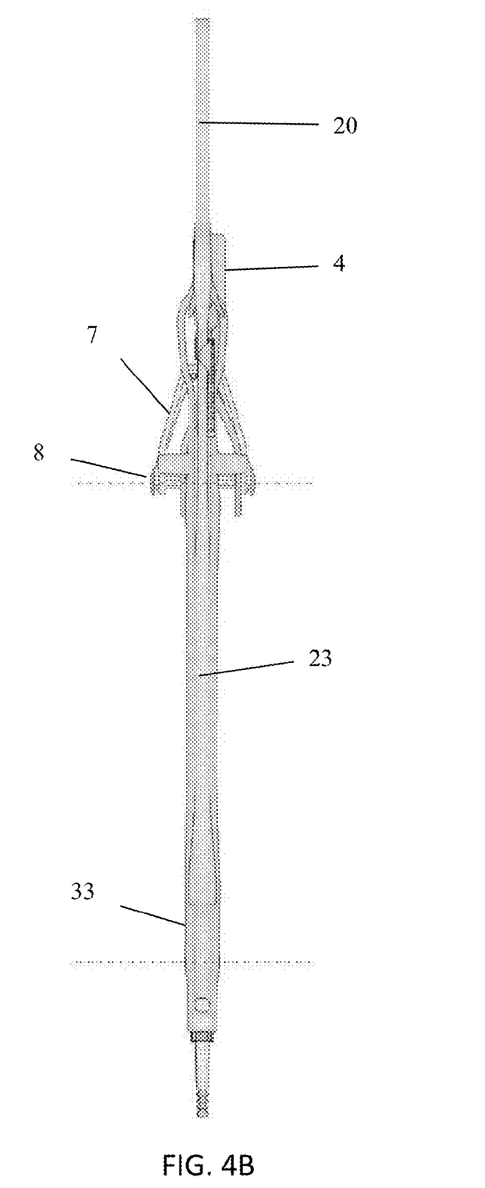

Another object of the present disclosure is to provide different direction of the rotation of said rotational bar 6 while using the actuator 4. FIG. 4A is directed to show the displacement of the actuator with respects to the pin 8. As shown the pin 8 comprises a length longer than the actuator length X2 with respect to the pin 8. For example the pin comprises a total length X3, and the actuator comprises an attachment portion 71 connected to the pin 8 comprising a second length X2. The difference between the lengths provides a space X1 for the displacement of the attachment portion 71. The displacement of said attachment portion 71 is enough to move the rack 51 from providing a rotational direction of the pinion to another direction (i.e. from counterclockwise to clockwise). For example, the space X'1 provided on FIG. 2A is positioned at a portion of the pin 8 different from the one showed in FIG. 4A. In fact the position of the rack 51 in FIG. 2A will provide clockwise motion of the pinion 600 and counterclockwise motion of the pinion 600 in FIG. 4A. It is important to understand that the movement of the actuator 4, more particularly the displacement of the attachment portion 71 is accomplish when the actuator is in the first position.

The actuator 4 further comprises an elastic or resilient member 7 coupled to the platform 4a. The elastic member 7 is configured to be compress from the first position to the second position. Subsequently as soon the platform 4a is release returns to its original position or first position. The elastic member 7 in the exemplary embodiment is a spring configured to recoil the platform to the first position. It is important to understand that any other resilient member can be used as long assists to recoil the platform 4a.

Further the first elongated body 33 extends from said first socket 30 towards said first tip 61. The first elongated body 33 comprises at least a set of walls 331,332 forming a clearance between each other, as shown in FIG. 4A. The clearance between the walls is enough to provide space for the rotational bar 6 and a portion of the second elongated body 23 to be located between them while the suturing device 1 is in use. In the instant case the suturing device is considered in use when the tips 61, 62 are grasping the needle N or in close contact.

In addition the second elongated element 2, as mentioned, includes a second elongated body 23, a second tip 62 at a distal end and a round contour including a second socket 20 at the proximal end. Further the elongated body 23 comprises a rotational bar support S. The rotational bar support S hold the rotational bar 6 in position with respect to the second elongated body 23 while provide bearing for the rotational movement of said rotational bar 6 when the actuator 4 interacts with the pinion 600. The rotational bar is mechanical coupled to the second tip 62, Therefore the rotational movement generated at the pinion is transferred to the second tip 62.

Figure 5:
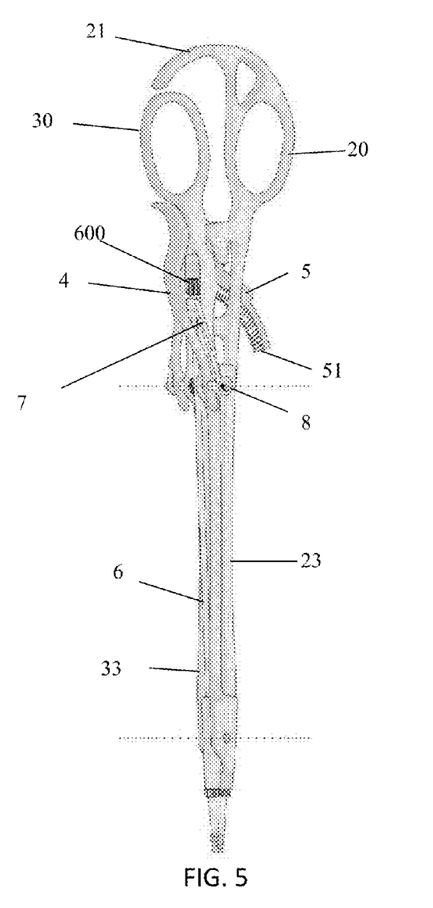
FIG. 5 shows a perspective view of the exemplary embodiment in accordance according with the principles of the present disclosure.
Figure 6:
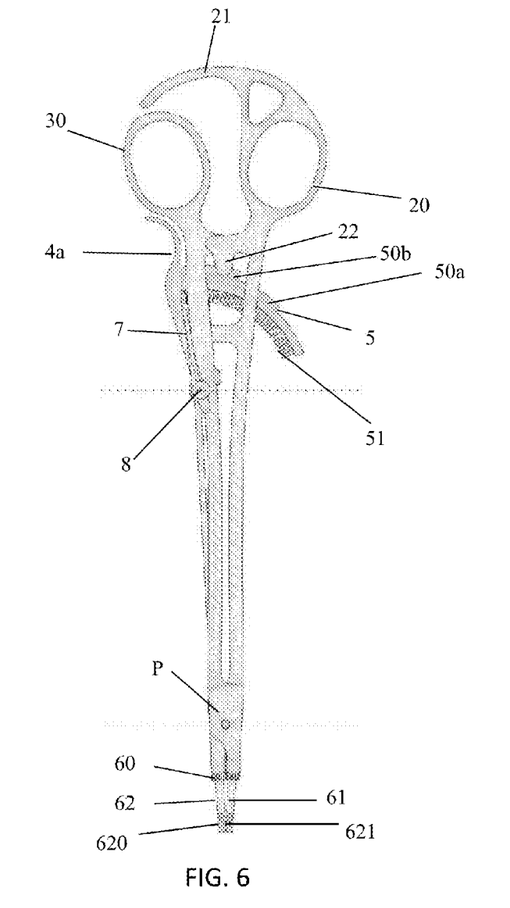
FIG. 6 shows a front view of the exemplary embodiment with actuator at second position in accordance according with the principles of the present disclosure.
Figure 7:
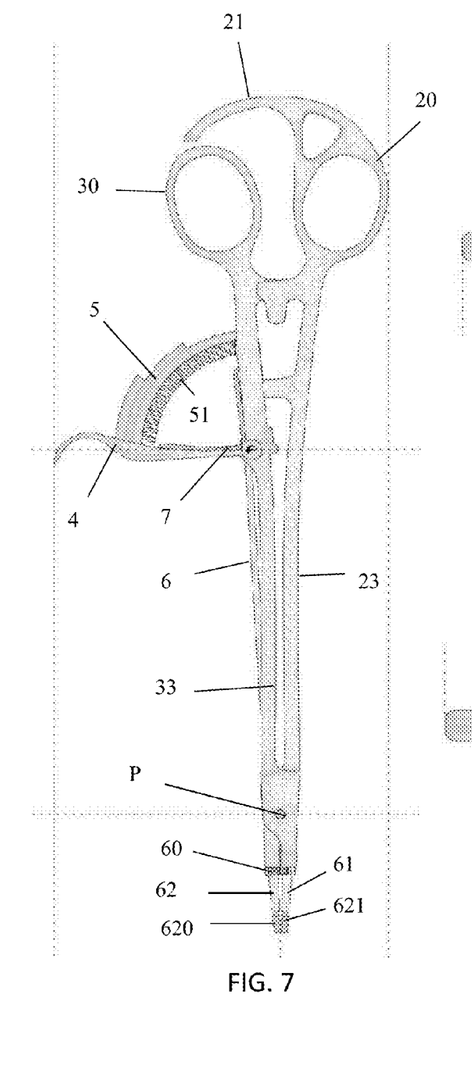
FIG. 7 shows a front view of the exemplary embodiment with actuator at a first position in accordance according with the principles of the present disclosure.
Figure 8:
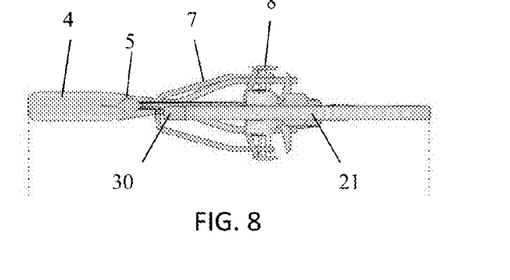
FIG. 8 shows a top view of the exemplary embodiment with actuator at a first position in accordance with the principles of the present disclosure.
Figure 9:
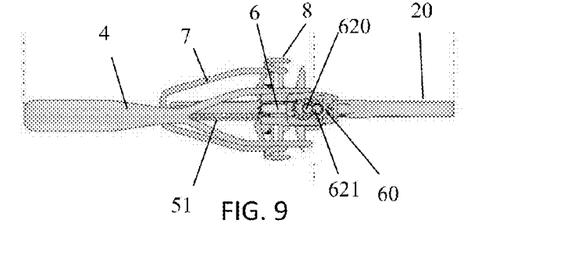
FIG. 9 shows a bottom view of the exemplary embodiment with actuator at a first position in accordance according with the principles of the present disclosure.
Figure 10:
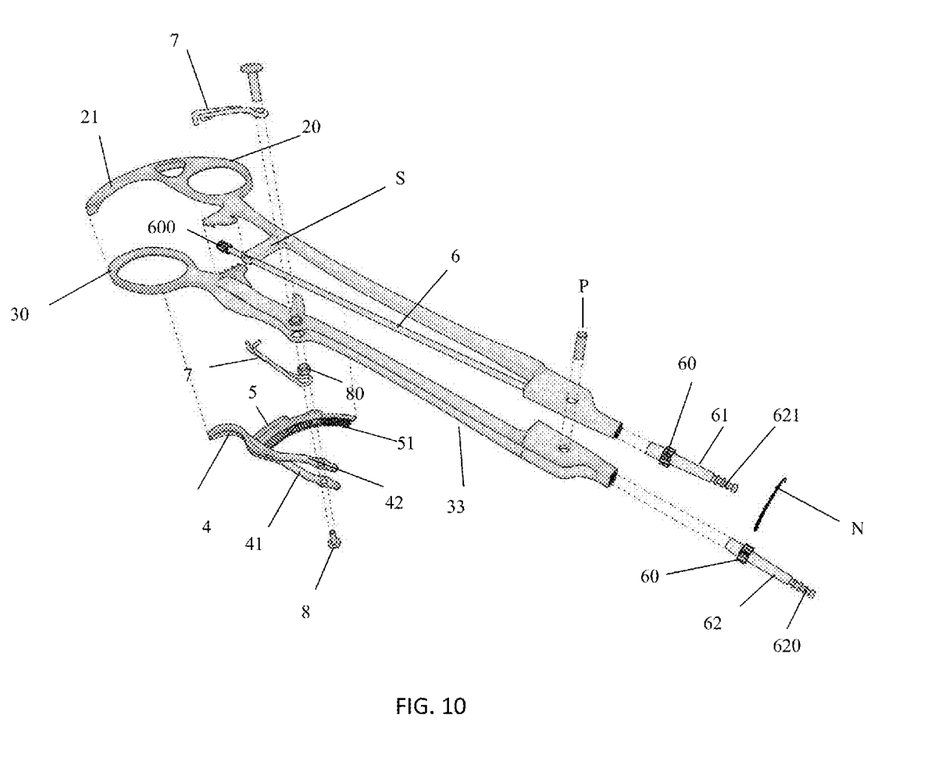
FIG. 10 shows an exploded view of the exemplary embodiment in accordance according with the principles of the present disclosure.

The first elongated element 2 and the second elongated member 3 are joint together at the box joint P. The box joint P serves as an intersection or pivot point between the first elongated element 3 and the second elongated element 2. As shown in FIG. 5 through FIG. 7, the second tip 62 and first tip 61 extends away from the box joint P.

FIG. 5 through FIG. 9 shows the grasping portion created by first tip 61 and second tip 62. In accordance with the exemplary embodiment the grasping force is preferred to be in an oblique manner, however the contact between tips 61, 62 maybe provided in other angles. Each tip 61, 62 is removable and comprises at least a distal end gear 60. In accordance with the principles of the present disclosure the gear is intended to assists to transmit the rotational movement of the second tip 62 connected to the rotational bar 6 to the first tip during the suturing procedures. It is important to understand that the gear serves as a rotation transmitting element for assisting to transferring the rotational motion from second tip 62 to the first tip 61, therefore any other rotation transmitting element could be used. Also each tip 62, 62 comprises at least contact distal end 620, 621 including grooves. The grooves or recess assists the increases the grasping force at the contact distal end 620, 621. The recess area may vary in order to assists to grasp different sizes of needles N. Further the tip 61, 62 may vary in length. The tip 61, 62 are made of any selected material capable to perform at least the functions herein mentioned. The selection of the material depends on the field the device is going to be employed. Also the contact distal end 620, 621 is preferred to have a surface that assist the performed action. For example, while using the device in a suturing process is preferred to have a distal end or contact distal end surface cover with a material, such as but not limited to silicon or rubber, that provide some friction over the needle in order to keep a constant displacement of said needle. Further the tips may include a layer of antibiotic or any other medical substance that assist the suturing and healing process of the patient. As mentioned before, the tips are removable and securely installed at the distal end of said elongated elements 2, 3. It is important to understand that the tips 61, 62 are removable and/or replaceable due to the need of grooves sizes for specific needles N or/and due to wear and tear problems, such as losing grasping force and/or avoiding particles losses due to friction.

Figure 11A:
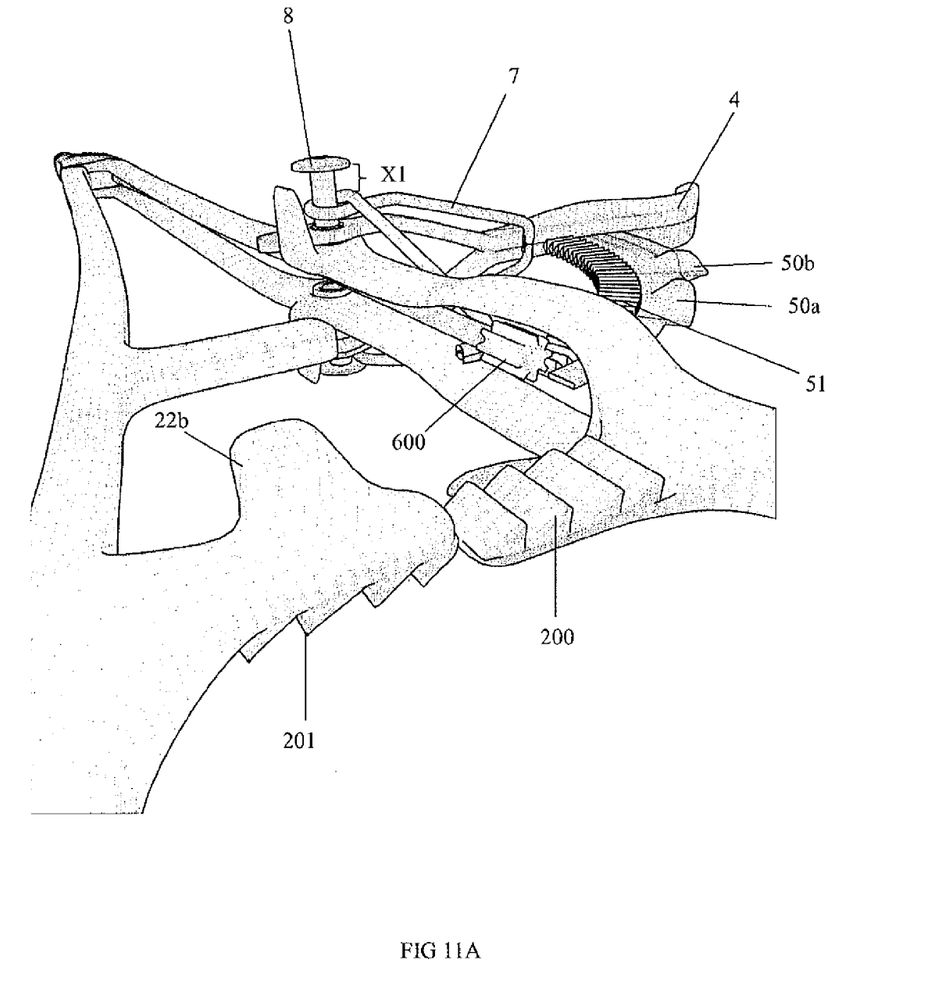
FIGS. 11A and 11B shows a detailed view of the exemplary embodiment of locking mechanism in accordance according with the principles of the present disclosure.
Figure 11B:
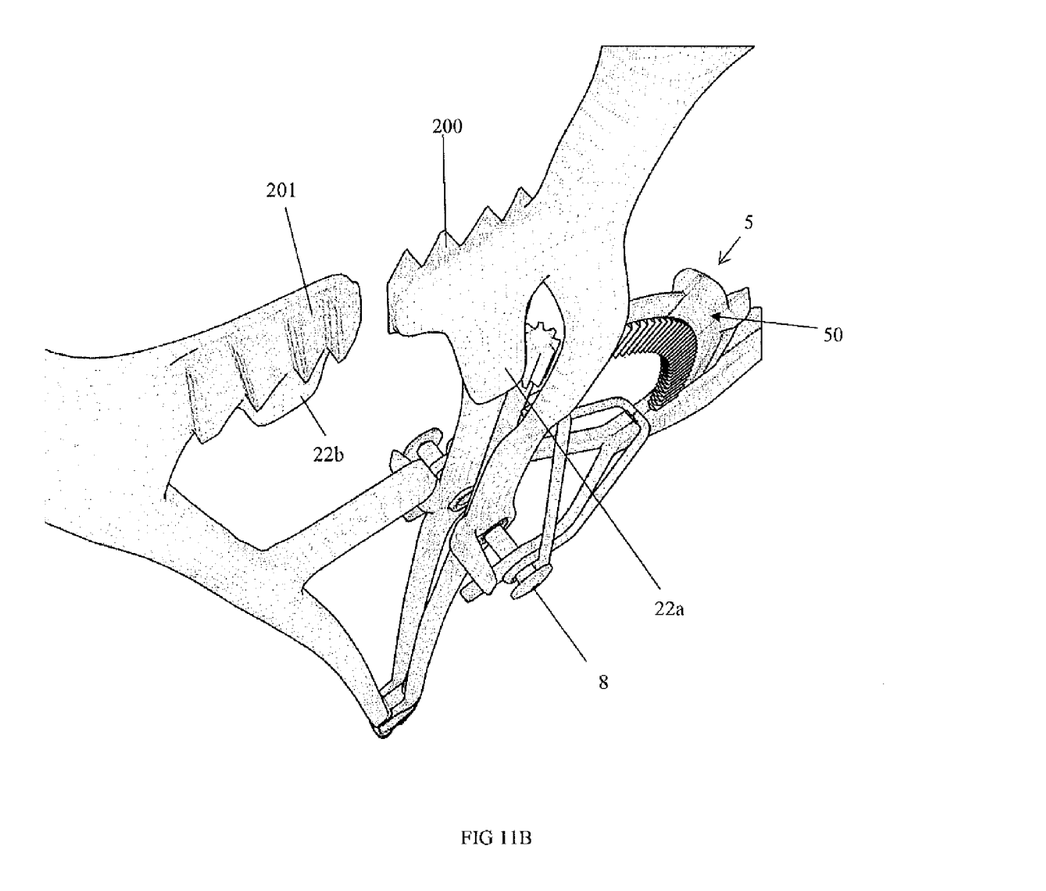

A locking mechanism 200 is located between the first elongated body 33 and second elongated body 23, as shown in FIGS. 11A and 11B. Each elongated body comprises a extended member with teeth interlocking with each other, in the form of a ratchet, assisting to hold the position between elongated bodies and consequently the distance between the first tips 62 and second tip 61. Further from said extended member 200, 201 comprise protrusion 22a, 22b. It is important to understand that the current device is usually on an open stage wherein the locking mechanism is not providing a constant distance between the first elongated element 3 and said second elongated element 2. While using the device 1 the user desires to close the gap between the elongated elements 2,3 in order to provide a constant distance between these two parts, consequently the first tip 62 and second tip 61 are in close contact grasping the needle N.

Another advantage of the present suturing device 1 is the unlocking mechanism, shown in FIG. 11a and FIG. 11b. The actuator 4, as previously disclosed, comprises a linear actuator including rack 51 and a flange 50. The flange 50 comprises at least two bumps 50a, 50b. The bump 50a, 50b are intended to assists with the unlocking mechanism by pushing up protrusions 22b, 22a. The protrusion 22b, 22a extends from the locking mechanism 200, 201. The bumps 50a, 50b are preferably located closer to the platform 4a. The purpose of providing the bumps 50a, 50b closer to the platform is to provide enough displacement of the rack 51 to rotate the pinion 600 before the bumps 50a, 50b interacts with the protrusions 22a, 22b. Therefore, when the actuator 4 is close to the second position the bumps 50a, 50b push up the protrusion 22a, 22b unlocking the rackets or locking mechanism 200, 201.

The disclosure is not limited to the precise configuration described above. While the disclosure has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

I claim:

1. A rotational driver comprising:
   interactive portions comprising a first elongated element and a second elongated element;
   a rotational transfer element including a rotational bar, wherein said rotational bar comprises a first bar distal end and a second bar proximal end;
   a resilient member;
   a locking mechanism;
   an unlocking mechanism;
   an actuator;
   wherein said first elongated element comprises a first detachable tip at a first distal end, a first proximal end and a first elongated body, wherein said first elongated body is between said first distal end and said first proximal end, wherein said first elongated body comprises a set of walls, wherein said set of walls comprises at least two walls spaced apart generating a clearance between said at least two walls, wherein said rotational bar fits between said clearance;
   wherein said second elongated element comprises a second detachable tip at a second distal end, a second proximal end and a second elongated body, wherein said second elongated body is between said second distal end and said second proximal end;
   wherein said first bar distal end is coupled to the second distal end, wherein said rotational bar extends between the actuator and the second distal end;
   wherein said actuator comprises a platform, a linear actuator and a radial displacement element, wherein said platform is fixed to said linear actuator and said radial displacement element is coupled to the second bar proximal end;
   wherein said linear actuator contacts said radial displacement element, wherein said linear actuator interacts with said radial displacement element to generate a rotational movement of the rotational bar about a longitudinal axis of the rotational bar; and wherein said unlocking mechanism comprises a flange; wherein said flange is configured to unlock said locking mechanism.

2. The rotational driver of claim 1, wherein said first detachable tip comprises a first contact distal end including at least a first recess; wherein said second detachable tip comprises a second contact distal end including a second recess; and wherein the first recess and the second recess are aligned.

3. The rotational driver of claim 1, wherein said rotational bar is attached to the second elongated body by a support element; and wherein said support element comprises a bearing for said rotational bar.

4. The rotational driver of claim 1, wherein said locking mechanism comprises at least two extended members with teeth for interlocking each extended member.

5. The rotational driver of claim 4, wherein said locking mechanism comprises protrusions.

\* \* \* \* \*